(12) United States Patent
Tsukamoto et al.

(10) Patent No.: US 7,003,356 B2
(45) Date of Patent: Feb. 21, 2006

(54) BATTERY TERMINAL SEALING AND SUPPORTING DEVICE AND METHOD

(75) Inventors: Hisashi Tsukamoto, Saugus, CA (US); Mikito Nagata, Valencia, CA (US); David DeMuth, Santa Clarita, CA (US); Michael Bowers, Venice, CA (US)

(73) Assignee: Quallion LLC, Sylmar, CA (US)

( * ) Notice: Subject to any disclaimer, the term of this patent is extended or adjusted under 35 U.S.C. 154(b) by 538 days.

(21) Appl. No.: 10/124,671

(22) Filed: Apr. 17, 2002

(65) Prior Publication Data

US 2003/0171783 A1    Sep. 11, 2003

Related U.S. Application Data

(60) Provisional application No. 60/362,902, filed on Mar. 8, 2002.

(51) Int. Cl.
*A61N 1/34* (2006.01)
(52) U.S. Cl. .................................... 607/57
(58) Field of Classification Search ............... 607/33, 607/55–57; 381/312, 323–330, 315; 352/242
See application file for complete search history.

(56) References Cited

U.S. PATENT DOCUMENTS

| | | | |
|---|---|---|---|
| 3,207,631 A | 9/1965 | Zaromb | |
| 3,537,907 A | 11/1970 | Wilson | |
| 3,782,814 A * | 1/1974 | Greenblatt | .......... 352/242 |
| 3,794,041 A | 2/1974 | Frei et al. | |
| 3,812,300 A | 5/1974 | Brander et al. | |
| 3,942,535 A | 3/1976 | Schulman | |
| 3,983,336 A | 9/1976 | Malek et al. | |
| 4,010,760 A | 3/1977 | Kraska et al. | |
| 4,022,952 A | 5/1977 | Fritts | |
| 4,075,400 A | 2/1978 | Fritts | |
| 4,119,103 A | 10/1978 | Jirak | |
| 4,197,850 A | 4/1980 | Schulman et al. | |
| 4,207,390 A | 6/1980 | Oehrlein et al. | |

(Continued)

FOREIGN PATENT DOCUMENTS

EP    0 178 769 A2    4/1986

(Continued)

OTHER PUBLICATIONS

R. Matthews, Instant Imaging Device Gives GPs Safe New Window into the Body, website: http://www.telegraph.co.uk/connected/main.jhtml?xml=/connected/2002/10/09/ecnxray06.xml.

(Continued)

*Primary Examiner*—George Manuel
(74) *Attorney, Agent, or Firm*—Gavrilovich, Dodd & Lindsey LLP

(57) ABSTRACT

The present invention is an efficient and economical battery sealing and supporting device and method. Among a variety of possible applications, the present invention may be utilized as an improved device and method that facilitates the use of cochlear stimulators designed to allow deaf and near deaf patients to experience the sensation of sound waves through electromechanical stimulation. The present invention eliminates the introduction of sweat, body fluid and other contaminants to the battery terminal connection area, which results in corrosion and eventually disables the connected device. Given its broad scope, the technology associated with the present invention is useful in medical and other areas, such as in military applications, hand-held computer and Internet systems and personal entertainment devices.

38 Claims, 9 Drawing Sheets

U.S. PATENT DOCUMENTS

| | | | |
|---|---|---|---|
| 4,232,679 A | 11/1980 | Schulman | |
| 4,311,206 A | 1/1982 | Johnson | |
| 4,314,008 A | 2/1982 | Blake | |
| 4,469,104 A | 9/1984 | Peers-Trevarton | |
| 4,495,917 A | 1/1985 | Byers | |
| 4,564,955 A | 1/1986 | Birch et al. | |
| 4,585,089 A | 4/1986 | Topholm | |
| 4,628,907 A | 12/1986 | Epley | |
| 4,741,979 A | 5/1988 | Faust et al. | |
| 4,784,141 A | 11/1988 | Peers-Trevarton | |
| 4,860,750 A | 8/1989 | Frey et al. | |
| 4,972,487 A * | 11/1990 | Mangold et al. | 381/315 |
| 5,025,550 A | 6/1991 | Zirbes et al. | |
| 5,047,044 A | 9/1991 | Smith et al. | |
| 5,084,699 A | 1/1992 | DeMichele | |
| 5,149,603 A | 9/1992 | Fleming et al. | |
| 5,193,540 A | 3/1993 | Schulman et al. | |
| 5,199,893 A | 4/1993 | Fussell | |
| 5,282,858 A | 2/1994 | Bisch et al. | |
| 5,304,214 A | 4/1994 | DeFord et al. | |
| 5,304,915 A | 4/1994 | Sanpei et al. | |
| 5,314,451 A * | 5/1994 | Mulier | 607/33 |
| 5,343,368 A | 8/1994 | Miller | |
| 5,370,669 A | 12/1994 | Daglow et al. | |
| 5,411,537 A | 5/1995 | Munshi et al. | |
| 5,411,538 A | 5/1995 | Lin | |
| 5,478,667 A | 12/1995 | Shackle et al. | |
| 5,535,097 A | 7/1996 | Ruben et al. | |
| 5,573,551 A * | 11/1996 | Lin et al. | 607/33 |
| 5,616,140 A | 4/1997 | Prescott | |
| 5,625,273 A | 4/1997 | Fehling et al. | |
| 5,629,678 A | 5/1997 | Gargano et al. | |
| 5,645,960 A | 7/1997 | Scrosati et al. | |
| 5,669,790 A | 9/1997 | Carson et al. | |
| 5,679,026 A | 10/1997 | Fain et al. | |
| 5,684,663 A | 11/1997 | Mitter | |
| 5,702,432 A | 12/1997 | Chen et al. | |
| 5,763,118 A | 6/1998 | Stafford et al. | |
| 5,766,793 A | 6/1998 | Kameishi et al. | |
| 5,814,095 A | 9/1998 | Muller et al. | |
| 5,833,603 A | 11/1998 | Kovacs et al. | |
| H1765 H | 12/1998 | O'Phelan et al. | |
| 5,898,356 A | 4/1999 | Gascoyne et al. | |
| 5,904,646 A | 5/1999 | Jarvik | |
| 5,919,215 A | 7/1999 | Wiklund et al. | |
| 5,951,595 A | 9/1999 | Moberg et al. | |
| 5,989,245 A | 11/1999 | Prescott | |
| 6,006,135 A | 12/1999 | Kast et al. | |
| 6,009,350 A | 12/1999 | Renken | |
| 6,010,800 A | 1/2000 | Stadnick et al. | |
| 6,039,685 A | 3/2000 | Bushek | |
| 6,040,082 A | 3/2000 | Haas et al. | |
| 6,074,774 A | 6/2000 | Semmens et al. | |
| 6,080,188 A | 6/2000 | Rowley et al. | |
| 6,087,809 A | 7/2000 | Gan et al. | |
| 6,102,739 A | 8/2000 | Murakami | |
| 6,120,502 A | 9/2000 | Michelson | |
| 6,127,438 A | 10/2000 | Hasegawa et al. | |
| 6,166,518 A | 12/2000 | Echarri et al. | |
| 6,172,482 B1 | 1/2001 | Eguchi | |
| 6,205,358 B1 | 3/2001 | Haeg et al. | |
| 6,210,824 B1 | 4/2001 | Sullivan et al. | |
| 6,242,893 B1 | 6/2001 | Freedman | |
| 6,252,762 B1 | 6/2001 | Amatucci | |
| 6,259,951 B1 | 7/2001 | Kuzma et al. | |
| 6,268,713 B1 | 7/2001 | Thandiwe | |
| 6,272,382 B1 | 8/2001 | Faltys et al. | |
| 6,273,904 B1 | 8/2001 | Chen et al. | |
| 6,278,258 B1 | 8/2001 | Echarri et al. | |
| 6,287,136 B1 | 9/2001 | Deutsch | |
| 6,308,101 B1 | 10/2001 | Faltys et al. | |
| 6,315,721 B1 | 11/2001 | Schulman et al. | |
| 6,327,502 B1 | 12/2001 | Johansson et al. | |
| 6,358,281 B1 | 3/2002 | Berrang et al. | |
| 6,400,991 B1 | 6/2002 | Kung | |
| 6,426,628 B1 | 7/2002 | Palm et al. | |
| 6,453,198 B1 | 9/2002 | Torgerson et al. | |
| 6,553,263 B1 | 4/2003 | Meadows et al. | |
| 6,564,807 B1 | 5/2003 | Schulman et al. | |
| 6,586,912 B1 | 7/2003 | Tsukamoto et al. | |
| 6,596,433 B1 | 7/2003 | Gudmundsson et al. | |
| 6,627,344 B1 | 9/2003 | Kang et al. | |
| 6,748,094 B1 * | 6/2004 | Tziviskos et al. | 381/330 |
| 2001/0016289 A1 | 8/2001 | Oura et al. | |
| 2001/0031909 A1 | 10/2001 | Faltys et al. | |
| 2002/0019669 A1 | 2/2002 | Berrang et al. | |
| 2002/0098410 A1 | 7/2002 | Leysleffer et al. | |
| 2004/0004464 A1 | 1/2004 | Tsukamoto et al. | |

FOREIGN PATENT DOCUMENTS

| | | |
|---|---|---|
| EP | 0 178 769 B1 | 4/1986 |
| EP | 0 806 806 A1 | 11/1997 |
| EP | 0 806 806 B1 | 1/2002 |
| JP | 55-111060 A2 | 8/1980 |
| JP | 55-119346 A2 | 9/1980 |
| JP | 55-119347 A2 | 9/1980 |
| JP | 56-028463 A2 | 3/1981 |
| JP | 56-162473 A2 | 12/1981 |
| JP | 56-162474 A2 | 12/1981 |
| JP | 57-072272 A2 | 5/1982 |
| JP | 57-138774 A2 | 8/1982 |
| JP | 59-063668 A2 | 10/1982 |
| JP | 58-082462 A2 | 5/1983 |
| JP | 58-097255 A2 | 6/1983 |
| JP | 58-128652 A2 | 8/1983 |
| JP | 58-209059 A2 | 12/1983 |
| JP | 59-090353 A2 | 5/1984 |
| JP | 59-128774 A2 | 7/1984 |
| JP | 60-025157 A2 | 2/1985 |
| JP | 60-068552 | 4/1985 |
| JP | 60-077350 A2 | 5/1985 |
| JP | 60-138847 | 7/1985 |
| JP | 61-114466 | 6/1986 |
| JP | 61-147473 A2 | 7/1986 |
| JP | 62-139245 | 6/1987 |
| JP | 62-154555 A2 | 7/1987 |
| JP | 01-140558 A2 | 6/1989 |
| JP | 02-054861 A2 | 2/1990 |
| JP | 02-075152 A2 | 3/1990 |
| JP | 02-148577 A2 | 6/1990 |
| JP | 04-206339 A2 | 11/1990 |
| JP | 03-263753 A2 | 11/1991 |
| JP | 05-101731 | 4/1993 |
| JP | 06-114036 A2 | 4/1994 |
| JP | 07-029563 A2 | 1/1995 |
| JP | 07-057719 | 3/1995 |
| JP | 07-094189 A2 | 4/1995 |
| JP | 07-130347 A2 | 5/1995 |
| JP | 07-130349 A2 | 5/1995 |
| JP | 07-240198 | 9/1995 |
| JP | 07-272702 A2 | 10/1995 |
| JP | 07-272706 | 10/1995 |
| JP | 07-272717 A2 | 10/1995 |
| JP | 08-106886 A2 | 4/1996 |
| JP | 08-138635 A2 | 5/1996 |
| JP | 08-241709 A2 | 9/1996 |
| JP | 09-237615 | 9/1997 |
| JP | 09-237616 A2 | 9/1997 |
| JP | 09-327447 A2 | 12/1997 |
| JP | 10-031997 A2 | 2/1998 |
| JP | 10-050348 A2 | 2/1998 |
| JP | 10-064548 A2 | 3/1998 |
| JP | 10-064549 A2 | 3/1998 |

| | | |
|---|---|---|
| JP | 10-139918 A2 | 5/1998 |
| JP | 10-279717 A2 | 10/1998 |
| JP | 11-069497 | 3/1999 |
| JP | 11-204151 A2 | 7/1999 |
| JP | 11-238518 A2 | 8/1999 |
| JP | 11-240970 A2 | 9/1999 |
| JP | 11-268118 A2 | 10/1999 |
| JP | 11-307081 A2 | 11/1999 |
| JP | 2000-100450 A2 | 4/2000 |
| JP | 2000-285873 A2 | 10/2000 |
| JP | 2001-043893 A2 | 2/2001 |
| JP | 2001-060465 A2 | 3/2001 |
| JP | 2001-060466 A2 | 3/2001 |
| JP | 2001-307688 A2 | 11/2001 |
| WO | WO 00/79625 A1 | 12/2000 |
| WO | WO 01/08578 A1 | 2/2001 |
| WO | WO 02/07598 A1 | 1/2002 |
| WO | WO 02/41755 A2 | 5/2002 |
| WO | WO 03/041208 A1 | 5/2003 |
| WO | WO 03/061032 A2 | 7/2003 |
| WO | WO 03/061032 A3 | 7/2003 |
| WO | WO 2004-014214 A2 | 2/2004 |
| WO | WO 2004/014214 A2 | 2/2004 |

OTHER PUBLICATIONS

G. MacLean et al., Preliminary Evaluation of Rechargeable Lithium-Ion Cells for an Implantable Battery Pack; 195, pp. 67-74, vol. 56.

Light Sciences Corporation web pages, www.lightsci.com.

International Search Report, PCT/US03/24168, International Filing Date Jul. 31, 2003; Mailing Date of Report Mar. 3, 2004.

* cited by examiner

BATTERY TERMINAL SEALING AND SUPPORTING DEVICE AND METHOD

CROSS-REFERENCE TO RELATED APPLICATIONS

This application claims the benefit of U.S. Provisional Application No. 60/362,902, filed Mar. 8, 2002.

BACKGROUND OF THE INVENTION

1. Field of Invention

The present invention relates to battery units that operate electrical and other small-scale devices. More particularly, the present invention relates to a device and method to seal and mechanically support the connection between a battery terminal and a medical device.

2. Description of the Prior Art

Batteries are commonplace in both everyday life and in scientific fields. As battery technology continues to make great strides, battery sizes have decreased, while battery power has increased. These advances render miniature batteries, particularly lithium ion batteries, indispensable in the field of biomedicine.

Typically, a battery is placed in a case having an opening that exposes the battery terminal. The battery case is then connected to a medical device via the exposed battery terminal. The integrity of the connection between battery case and medical device is critical for proper function and safety.

In one application of this technology, batteries are used in conjunction with medical devices, such as neurological stimulators, that are implanted in a human patient. In such applications, the integrity of the connection between battery and medical device has even further importance. A connection failure may result in medical device malfunction giving rise to potentially devastating results. Accordingly, the connection must not only be mechanically sound, but the connection must also prevent the introduction of foreign matter, such as body fluids and other contaminants, that may compromise the electrical connection.

More particularly, one such application involves the use of cochlear stimulators that allow deaf and near deaf patients to experience the sensation of sound waves through electromechanical stimulation. One type of cochlear stimulator comprises an implantable portion and an external portion that interacts with the implanted portion through the skin. The external portion of the cochlear stimulator comprises a housing for electronics designed to accept a battery terminal. An external encased battery mounted to the terminal acceptor powers the cochlear stimulator. As such, the cochlear stimulator battery can be replaced easily by the patient and without the need for a surgical procedure. Because these batteries typically have a life of only three to twelve hours before they need to be recharged, the batteries may be detached and reattached one to several times a day. Furthermore, these devices are often worn by children and the elderly. Therefore, their battery connection must be both easy to work and robust.

A particular problem associated with cochlear stimulators is battery terminal corrosion. When sweat, bodily fluids and other contaminants come in contact with the battery terminal, corrosion occurs that eventually disables the cochlear stimulator. In some designs, the battery and electronics, including a transmitter, are located in a single housing that may be worn on a belt. In other designs, the batteries and electronics are in two separate housings, and the entire external portion of the cochlear stimulator is worn behind the ear, greatly increasing the exposure to sweat. Further, because cochlear stimulators typically require high voltages, often from lithium ion batteries, corrosion of the battery terminal connection is accelerated[1]. As such, an effective, efficient solution is needed for this problem. To date, no such solution has been found.

[1] Indeed, zinc-based batteries of 1.5 volts have now been replaced with lithium ion batteries of 4 volts and greater.

For example, one attempt to remedy corrosion is the use of gold plated, platinum plated or iridium plated battery terminals. These types of battery terminals are designed to better withstand corrosion. However, this approach is expensive and will only delay corrosion, not prevent it. Another approach is to incorporate a sacrificial electrode, often of zinc construction, to offset the corrosive effect. Once again, incorporating an additional electrode is costly and inefficient, and in any case, will not prevent corrosion after prolonged use and exposure to contaminants.

Other attempted remedies similarly fail to address the current needs. For example, the reference to Oehrlein et al., U.S. Pat. No. 4,207,390, designed primarily for automotive batteries, is limited to battery side terminal assemblies. This reference discloses a sealing means (in one embodiment an o-ring) that prevents electrolyte from reaching the battery side terminals. As such, a complete seal is not disclosed, but rather, a protection means limited to only the terminal area of a battery. Further, this reference incorporates numerous and intricate elements such as a female threaded connector, a lug, a collar, a head portion with recessed portion, a sealing means, a base portion having a series of keys, and a depending skirt. Naturally, the failure of any of these elements or their respective interconnection would result in leakage. Thus, this attempted remedy is costly, impractical and difficult to maintain.

The reference to Brander et al., U.S. Pat. No. 3,812,300, designed primarily to prevent sound leakage from a connection between a receiver and an acoustical load, discloses the use of solder joints in conjunction with an o-ring to complete the acoustical coupling rendering this reference impractical for use with modem cochlear devices. There is no teaching of a seal for preventing intrusion of bodily fluids. Similarly, the reference to Kraska et al., U.S. Pat. No. 4,010,760, incorporates an o-ring, however, the seal (which does not isolate the power source) further incorporates a screw tight fitting thereby missing the goal of simple removal.

The reference to Malek et al., U.S. Pat. No. 3,983,336, discloses the use of an o-ring, but principally for the purpose of facilitating rotation of the sound inlet passage of an outdated hearing aid. Similarly, the reference to Birch et al., U.S. Pat. No. 4,564,955, incorporates an o-ring, however, for the primary purpose of providing rotation friction to dispose the device in various positions. Furthermore, the seal in this reference does not provide a simplified solution to disconnect and connect the device components, nor does it provide an efficient means to change the o-ring after continued use.

Similar limitations are found in other U.S. references. For example, the reference to Fussell, U.S. Pat. No. 5,199,893, discloses a seismic connector for plugging geophones into a leader cable and having an o-ring, however, with the further limitations of a second recessed structure and a complicated and inaccessible connection means. The reference to Murakami, U.S. Pat. No. 6,102,739, incorporates the use of a resin chemical process to accomplish the seal which is wholly impractical for modem cochlear devices. Finally, the reference to Deutsch, U.S. Pat. No. 6,287,136 B1, discloses a complex connection means not appropriate to address present needs.

Turning to foreign references, the reference to Sanyo Electric Co. Ltd., Japan, JP7240198A2, discloses use of an o-ring to seal the terminal area of a battery used to power an electrical appliance. While far simpler than the Oehrlein et al. reference, the Sanyo reference provides little to no means of mechanically supporting the assembled battery and electric appliance. Designed for larger scale operations, the Sanyo reference is not practical for smaller scale operations such as wearable and/or implantable medical devices used in conjunction with lithium ion batteries.

Another reference to Sanyo Electric Co. Ltd., Japan, JP7272706A2, discloses a waterproof structure having a flange for a portable electric appliance. While the flange provides some mechanical support, this element is impractical to provide the support needed for a cochlear stimulator or like device. Similar limitations are found in the reference to Matsushita Electronic Ind. Co. Ltd., Japan, JP9237615A2, that discloses a device for providing liquid and air protection to a lead-acid battery.

The reference to Shin Kobe Electric Mach. Co. Ltd., Japan, JP7057719A2, discloses a battery terminal sealing part in which an o-ring is eliminated, for lead-acid battery terminals. Two other references to Shin Kobe Electric Mach. Co. Ltd., Japan, JP61114466A2 and JP60138847A2, disclose sealing parts limited to cylindrical batteries. Also, the complexities implicated in the Shin Kobe references, such as a movable o-ring, render them inefficient and impractical for medical devices.

Nor is the reference to Nippondenso Co. Ltd., Japan, JP5101731A2, disclosing a connecting terminal, practical for medical applications. While water resistance and insulation is provided by this reference, the lack of mechanical support for devices connected to the battery terminal renders this reference inappropriate for miniature, wearable and/or implanted devices.

Other references similarly fail to address current needs in medical device battery technology. The reference to Yuasa Battery Co. Ltd., Japan, JP62139245A2, discloses a sealing method for a storage battery. However, the use of setting resins renders this reference impractical for removable batteries used in conjunction with medical devices.

The reference to Furukawa Battery Co. Ltd., The Honda Motor Co. Ltd., Japan, JP60068552A2, discloses a sealing device for a storage battery terminal. While this reference may provide some level of insulation and sealing, its primary goal is to address shock and vibration.

Many of the electrical connection sealing mechanisms in the prior art lack the ability to provide mechanical support and require additional means to provide necessary mechanical support to render such mechanisms practical for use between a medical device and battery unit. Other inventions address the need for mechanical support; however, the manner of achieving such support is often needlessly complicated and impractical. Indeed, the means for supporting implantable medical devices proposed in the prior art generally require adjustments, in some cases requiring a physician or other medical practitioner to replace the battery unit. These limitations are both expensive and inconvenient.

A number of implantable devices use seals of some type to prevent blood leakage into the device; however, these inventions are not meant for frequent attachment and detachment, particularly by the patient. Two implantable devices that use seals are the cardiac pacemaker and defibrillator in which a header is permanently affixed to a hermetically sealed housing that contains the battery and electronics, which includes a microprocessor and timing circuitry. Flexible lead connectors are inserted into connector ports in the header, with the electrodes extending into or about the patient's heart. Seals may be provided, located on the lead connectors, within the connector ports, or both, to seal the device against intrusion by bodily fluids. The leads are attached by the surgeon at implant, usually via set screws, and then left in place for the life of the device, typically five to ten years or more. When the battery is depleted, the device is surgically accessed, the set screws are loosened, and the flexible leads are unplugged from the device and reconnected to a new device. Examples of such devices include those described in U.S. Pat. No. 6,327,502 B1 to Johansson et al., U.S. Pat. No. 6,039,685 to Bushek, U.S. Pat. No. 5,669,790 to Carson et al., and U.S. Pat. No. 5,919,215 to Wiklund et al.

Because various sizes and configurations of leads are available for cardiac pacemakers and defibrillators, implantable adaptors have become available to allow the pacemakers and defibrillators to be used with various leads having different connectors. These adaptors are detachably connectable to the header of the device on one side and to the leads on the other side. However, neither the adaptor-to-device connection nor the adaptor-to-leads connection is designed to be detached by the patient on a daily basis. Examples of such devices include U.S. Pat. No. 5,679,026 to Fain et al. and U.S. Pat. No. 6,006,135 to et al. To mechanically connect the adaptor to the device and the leads to the adaptor, Fain et al. uses set screws, requiring a hex wrench to loosen and tighten, which would be too difficult and time consuming for use in the present application. Kast et al. describes several connection devices, including a latching assembly, which requires a hex wrench to remove, and complex spring clip assemblies that are likely to fail if used daily.

The prior art includes implantable medical devices that have replaceable batteries; examples are found in U.S. Pat. No. 5,314,451 to Mulier and U.S. Pat. No. 5,411,538 to Lin. While mechanical support means are disclosed in these references, the support means are relatively complex and cumbersome to use and are not intended for daily disconnection and reconnection. In Mulier, the mechanical support means requires at least two securing locations, namely, the location of the electrical connector(s) and the location of a pin. With such a configuration, the requirement of at least two distinct securing locations needlessly complicates the manufacturing of this device and adds to the overall cost. Second, because the electrical connector is positioned far from the pin, removal of the battery unit is cumbersome in that both ends of the battery unit must be pulled out simultaneously and with equal force to avoid misalignment jams. Misalignment can also result in the breaking of an electrical connector or pin. In both Mulier and Lin, using four set screws, cap screws, or Sidelock™ connectors renders the removal and replacement of a battery time consuming and impractical if done daily for recharging. The patient who does not have sufficient manual dexterity to use small tools will be precluded from replacing the battery without outside help. Furthermore, the grommets, or septa, used to access the set screws may be prepierced or pierceable with a screwdriver, and may be self-sealing or may require sealing with room temperature vulcanizing (RTV) adhesive. The grommets themselves present potential leakage paths, and if penetrated daily, would quickly wear out. Replacing the grommets would require sending the unit to a lab or manufacturing facility. These problems severely limit the practicality and usefulness of the inventions of Mulier and Lin in an application that requires frequent detachment and reattachment of the battery. Lastly, the inventions of Mulier and Lin are intended for implant, and therefore, like the other implantable devices described above, use expensive implantable materials. As such, it is desirable to have a device that provides a simple, inexpensive, reliable, robust connection and sealing mechanism and that addresses the problems found in the prior art in an efficient and effective manner. However, and in view of the foregoing, nothing in the prior art addresses these deficiencies.

SUMMARY OF THE INVENTION

The present invention is an efficient, economical device and method that facilitates the use of battery-powered, miniature devices. More specifically, the present invention is a device and method that enables effective and prolonged use of cochlear stimulators designed to allow deaf and near deaf patients to experience the sensation of sound waves through electromechanical stimulation. One type of a cochlear stimulator comprises an implantable portion and an external portion that interacts with the implanted portion through the skin. The external portion of the cochlear stimulator comprises a housing for electronics designed to accept a battery terminal. Thus, an external encased battery mounted to the external portion of the cochlear stimulator powers the cochlear stimulator. As such, the battery powering the cochlear stimulator can be replaced easily and without the need for invasive medical procedure.

A particular problem associated with the use of cochlear stimulators and related medical devices is battery terminal corrosion. When the battery terminal comes into contact with sweat, bodily fluids, and other contaminants, corrosion results. Left unchecked, corrosion will eventually disable a cochlear stimulator. Further, because cochlear stimulators typically require high voltages, often from lithium ion batteries, corrosion is accelerated rendering this a serious problem.

A related problem is medical device stability. Because, in this case, the cochlear stimulator remains implanted in a patient, the external battery must be firmly connected in such a way as to avoid disconnection resulting in battery loss, medical device failure, and connection seal compromise. Thus, in addition to ensuring a complete seal of the connection area between a battery and a medical device, the connection must also be mechanically sound.

The present invention addresses these needs in an effective and efficient framework. The use of a strategically positioned o-ring in one preferred embodiment of the present invention ensures a complete seal. Additionally, the utilization of a male insert and a female acceptor provides the necessary mechanical stability. In another preferred embodiment of the present invention, the use of miniature o-rings and/or a plate seal ensures a complete seal. A slide system and a sheath provide the necessary mechanical support in this preferred embodiment.

The advances set forth in the present invention may also be used outside the field of medical devices. For example, the present invention may be used for military and police applications, such as for personal communication devices. The present invention may also be used for portable computer and/or Internet hand-held device systems that require a protective seal and mechanical stability. Finally, the present invention may be used for personal entertainment devices leading to the ability to listen to music, news and other communications via a battery-powered device placed near a human ear or resting on the frame of a pair of glasses.

It is therefore an object of the present invention to provide a new and improved battery terminal sealing device and method that have all the advantages of the prior art, yet none of the disadvantages. It is a further objective of the present invention to provide a new and improved battery terminal sealing device and method that may be easily and efficiently manufactured and marketed. It is a further object of the present invention to provide a battery terminal sealing device that is of durable and reliable construction.

It is yet a further object of the present invention to provide a new and improved battery terminal sealing device and method that is of low cost to manufacture with regard to both materials and labor, and that, accordingly, is then susceptible of low prices of sale to the consuming public, thereby making the present invention economically available to the buying public.

Yet another object of the present invention is to provide a new and improved battery terminal sealing device and method that is portable and can be used in a myriad of locations and situations, both medical and beyond.

The present invention may be better understood by referring to the following Detailed Description, which should be read in conjunction with the accompanying drawings. The Detailed Description of a particular preferred embodiment, described below, is intended to be a particular example, and not a limitation.

BRIEF DESCRIPTION OF THE DRAWINGS

The accompanying drawings, which are incorporated in and constitute a part of the specification, illustrate presently preferred embodiments of the present invention, and together with the preceding general description and the following Detailed Description, explain the principles of the present invention.

In the drawings.

DETAILED DESCRIPTION OF THE INVENTION

Embodiments consistent with the present invention address the need for an effective and efficient battery terminal sealing device and method. While the prior art attempts to address this need, only the present invention provides a device and method that incorporate all desirable characteristics. The device and method described herein may be implemented in a variety of manners and conditions. Accordingly, the description of particular embodiments herein is intended only for the purposes of example, and not as a limitation.

Figure 1:
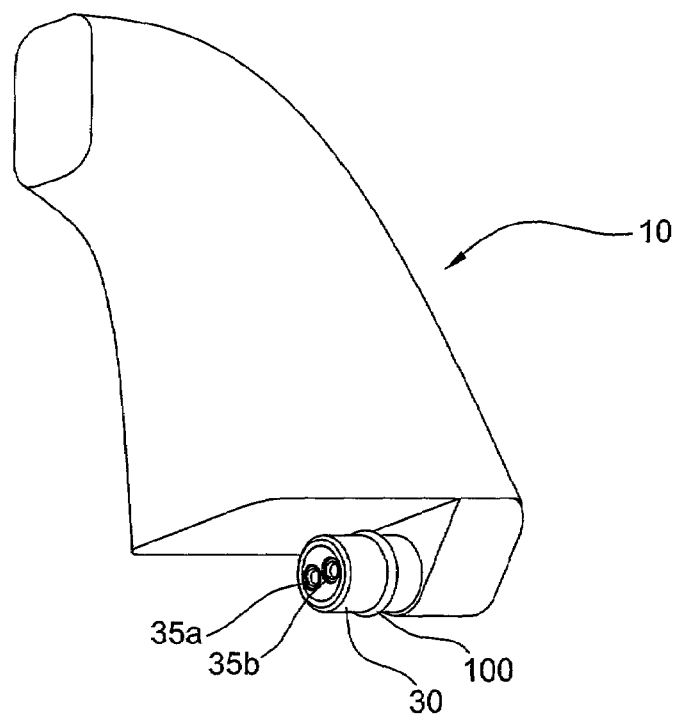
FIG. 1 is a perspective view of a cochlear stimulator of a preferred embodiment of the present invention.
Figure 2:
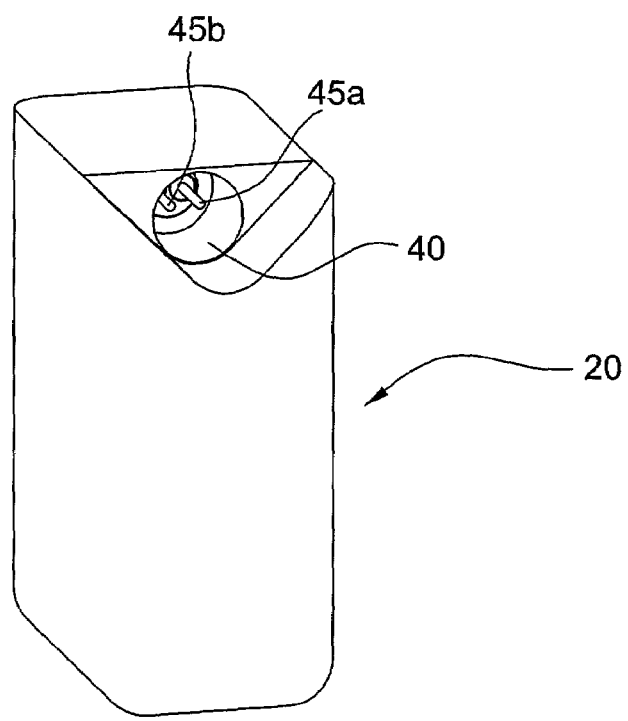
FIG. 2 is a perspective view of a battery unit of a preferred embodiment of the present invention.

FIGS. 1 and 2 illustrate a cochlear stimulator (10) and a battery unit (20), respectively, of a preferred embodiment of the present invention. The cochlear stimulator (10) is designed to efficiently impart mechanical and electrical signals to a deaf or near deaf patient. The cochlear stimulator (10) comprises a male insert (30) having two terminal sockets (35a, 35b). The male insert (30) further comprises an o-ring (100) positioned along the periphery. The strategic positioning of the o-ring (100) is designed to fully seal the connection between the cochlear stimulator (10) and the battery unit (20) in order to prevent the introduction of body fluids and other contaminants. For purposes of illustration, the male insert (30) is cylindrical in shape. However, other shapes and configurations can be used with equal suitability and success. In a preferred embodiment, both the battery unit housing and the cochlear stimulator housing are made of plastic.

Battery unit (20) comprises an internal battery (not shown) housed in a battery case. The battery unit (20) connects with the cochlear stimulator (10) via the insertion of the male insert (30) into the female acceptor (40), the latter of which is constructed integral with the battery unit (20). Housed within the female acceptor (40) are two terminal posts (45a, 45b) that are inserted into the two terminal sockets (35a, 35b), respectively. As such, the insertion of the male insert (30) into the female acceptor (40) provides mechanical stability for the assembled cochlear stimulator (10) and battery unit (20), while the insertion of the terminal posts (45a, 45b) into the terminal sockets (35a, 35b) provides the electrical connection that powers the cochlear stimulator (10).

Note that although the preferred embodiment has terminal posts in the acceptor and terminal sockets in the male insert, in an alternative embodiment (not shown), the terminal posts may be on the male insert and the terminal sockets in the female acceptor. Likewise, although the acceptor is illustrated as being on the battery unit and the male insert is illustrated as being on the cochlear stimulator, these features may also be reversed.

One or more o-rings may be used to provide added protection. When more than one o-ring is used, they are preferably slightly spaced apart from each other. Furthermore, the o-ring may be adhered to the male insert, such as by insert molding or adhesive bonding; alternatively, the o-ring may be removable for replacement when it wears out. In one embodiment, the o-ring resides in a slight recess, similar to the optional groove (61) shown in the embodiment of FIG. 7, or may remain in place by friction, or may be free to slide down to the base of the male insert for sealing against the entrance to the female acceptor. In an alternative embodiment (not shown), the seal may be located within the female acceptor, preferably adhered or within an optional groove.

Accordingly, the use of a strategically positioned o-ring (100) in the present invention ensures a complete seal of the connection between the cochlear stimulator (10) and the battery unit (20), including both battery terminal posts and both sockets, from external contaminants. When assembled, the o-ring (100) may seal against either the surface of the female acceptor (40), against the entrance of the female acceptor (40), or both. Additionally, the utilization of a male insert (30) and a female acceptor (40) provides the necessary mechanical stability to maintain the assembly in a secure manner. An additional locking feature, not shown, may be provided for added security. The sealing, stabilization, and optional additional locking are accomplished in one motion, simply by inserting the male insert (30) into the female acceptor (40).

One of the benefits of this configuration of the invention is that all of the feedthrough components of both the battery unit (20) and the cochlear stimulator (10) are on the "dry side" of the seal. On the "wet side" of the seal, the battery unit and the cochlear stimulator housings each can be made of a single material, molded, welded, or otherwise sealed, without joints between dissimilar materials being exposed.

Figure 3:
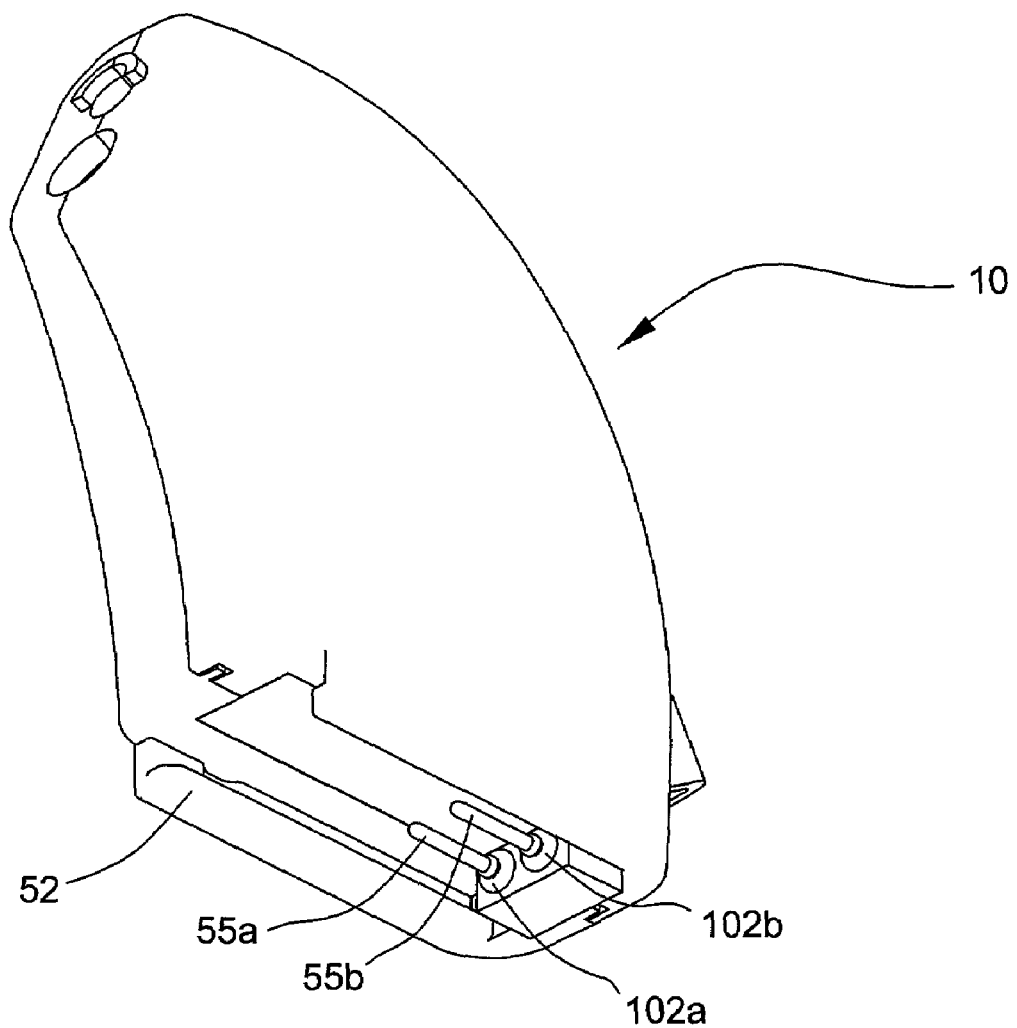
FIG. 3 is a perspective view of a cochlear stimulator of an alternative preferred embodiment of the present invention.
Figure 4:
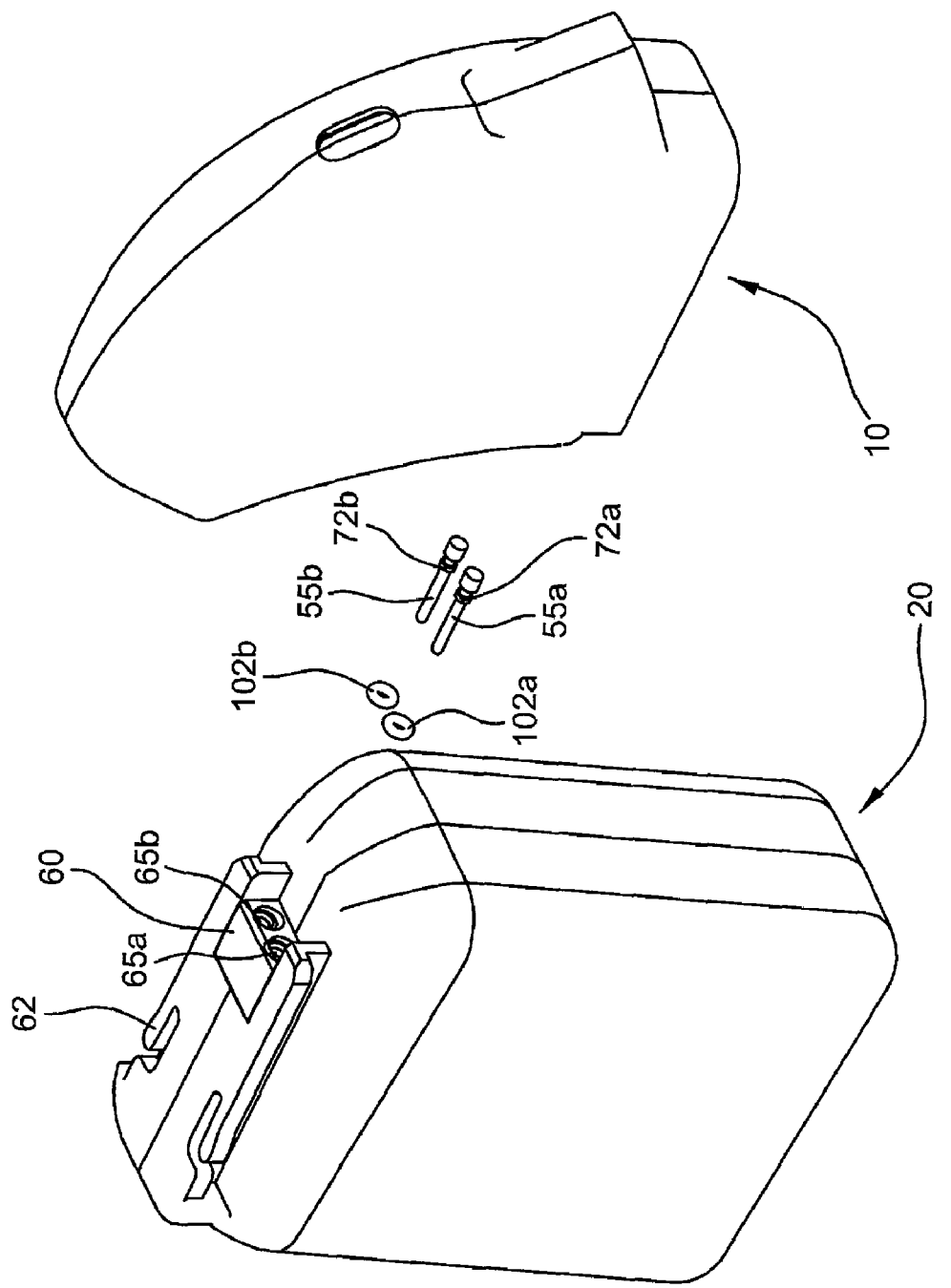
FIG. 4 is an exploded view of a cochlear stimulator and battery unit illustrating an alternative preferred embodiment of the present invention.
Figure 5:
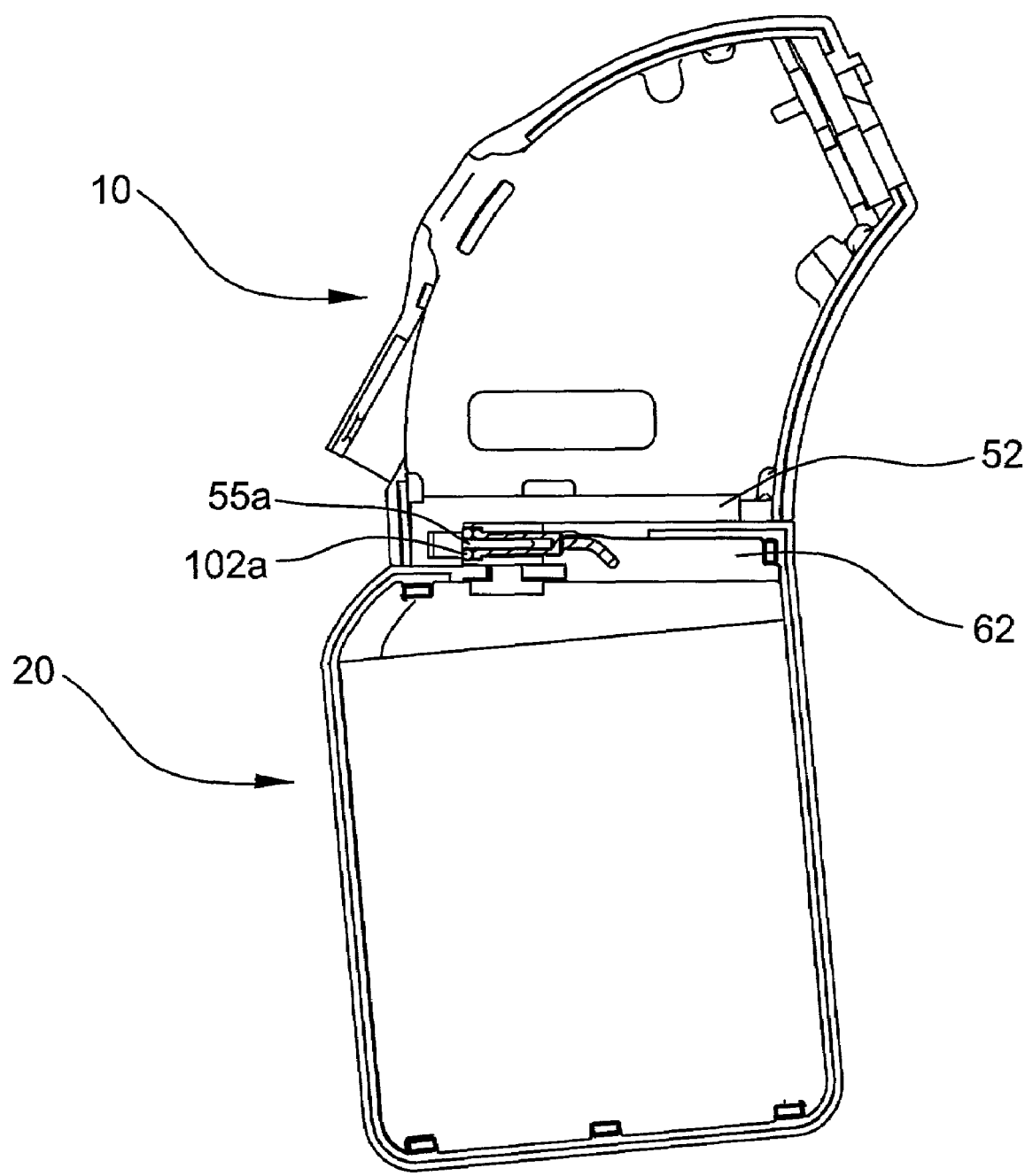
FIG. 5 is a side section view of an assembled cochlear stimulator and battery unit of an alternative preferred embodiment of the present invention.

FIGS. 3–5 depict an alternative preferred embodiment of the present invention. Here, a female slide (52) is formed integral with the cochlear stimulator (10). Two terminal posts (55a, 55b), designed to accept an electrical charge from the battery unit (20), are connected to the cochlear stimulator (10). Two miniature o-rings (102a, 102b) are slid onto the base portion of the two terminal posts (55a, 55b), respectively, to protect the terminal sockets (65a, 65b), and therefore the battery unit (20), from external contaminants.

FIG. 4 is an exploded view of the alternative preferred embodiment of the present invention. The cochlear stimulator (10) is illustrated along with two terminal posts (55a, 55b), two miniature o-rings (102a, 102b), and the battery unit (20). In this embodiment, a male slide (62) is formed integral with the battery unit (20). The battery unit (20) houses two terminal sockets (65a, 65b) designed to receive the two terminal posts (55a, 55b) each having a miniature o-ring (102a, 102b respectively). The two terminal sockets (65a, 65b) may be positioned within a housing (60) mounted within the male slide (62). Alternatively, housing (60) may be formed integral with the battery unit (20).

In an alternative embodiment, the miniature o-rings (102a, 102b) may be substituted by a plate seal (103) (FIGS. 12 and 13), such as a rectangular piece of rubber with a pair of holes therethrough for installation over the terminal posts (55a, 55b). The miniature o-rings and/or plate seal may be bonded, molded, or otherwise adhered to either the cochlear stimulator (10) or to the battery (20) or to neither. As shown in FIG. 4, the terminal posts (55a, 55b) may have capture features (72a, 72b) to keep the miniature o-rings (102a, 102b) or the plate seal (103) from separating from terminal posts (55a, 55b).

FIG. 5 is a side section view showing the components of FIG. 4 assembled. The preferred positioning of terminal post (55a) and corresponding miniature o-ring (102a) on the cochlear stimulator (10) is illustrated in FIG. 5. The slide system (52, 62) provides the necessary mechanical support in this alternative preferred embodiment.

Figure 6:
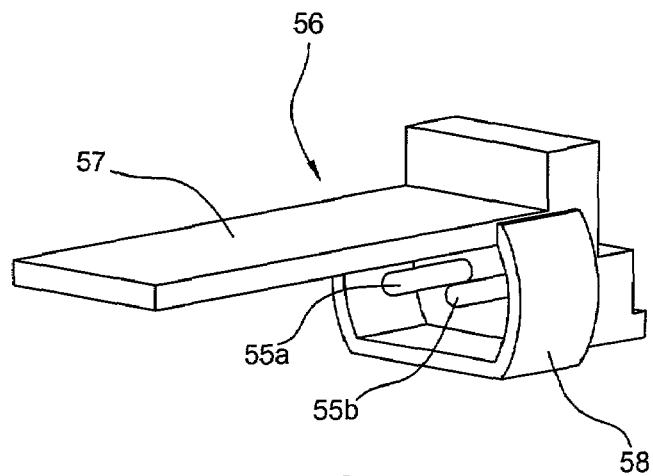
FIG. 6 is a perspective view of the sheath of an alternative preferred embodiment of the present invention.

FIGS. 6–9 depict another alternative preferred embodiment of the present invention. FIG. 6 illustrates a perspective view of a portion of the cochlear stimulator (10), sheath (56), comprising an elongated member (57) and a hub portion (58) with two terminal posts (55a, 55b). When assembled, a portion of the battery unit (20) mates with the hub portion (58), and the elongated member (57) rests against the battery unit (20).

Figure 7:
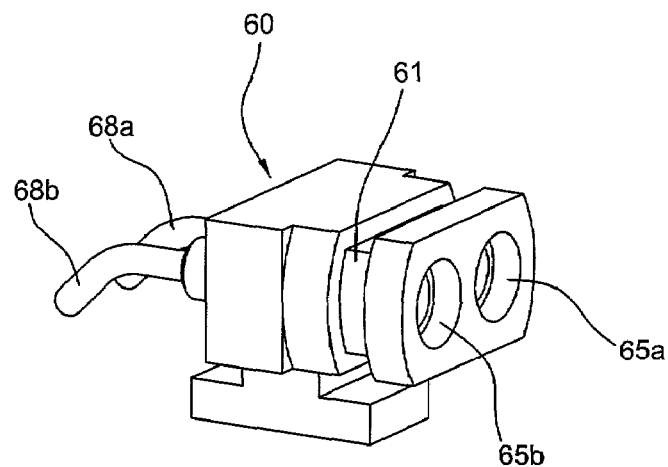
FIG. 7 is a perspective view of a housing of an alternative preferred embodiment of the present invention.

FIG. 7 is a perspective view of the housing (60) of the battery unit (20) modified to have an optional groove (61). The terminal sockets (65a, 65b) positioned at one end of the housing (60), correspond respectively to two connector pins (68a, 68b). Thus, once the two terminal posts (55a, 55b) are inserted into the two terminal sockets (65a, 65b), respectively, electrical charge is carried from the battery unit (20) to the two connector pins (68a, 68b), and thereby to the two terminal sockets (65a, 65b). The electrical charge is then transferred onto the two terminal posts (55a, 55b) that, in turn, are connected to and power the cochlear stimulator (10).

Figure 8:
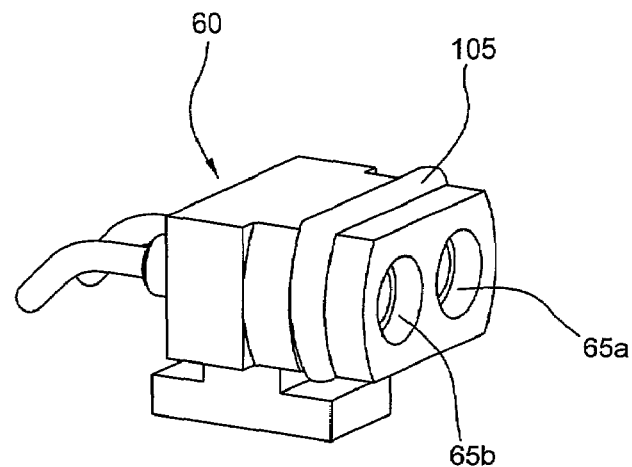
FIG. 8 is a perspective view of the housing of FIG. 7 illustrating a gasket installed.

FIG. 8 illustrates the housing (60) of the battery unit (20) having a gasket (105) that is installed on the periphery of the housing (60), within groove (61). The gasket (105) is designed to seal the connection between the housing (60) and the hub portion (58) of the sheath (56) (FIG. 6).

Figure 9:
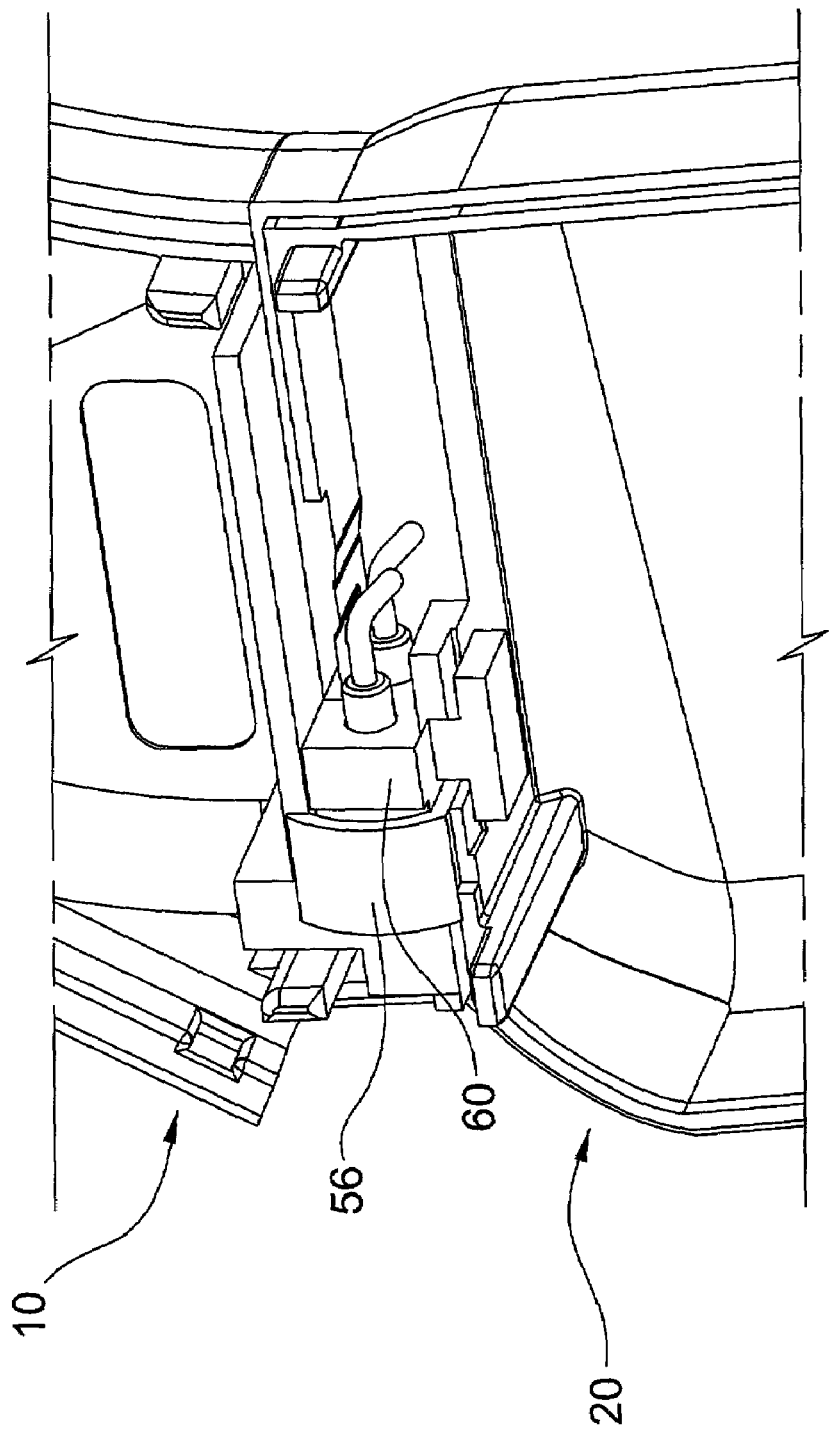
FIG. 9 is a section view of an assembled cochlear stimulator and battery unit of an alternative preferred embodiment of the present invention.

FIG. 9 is a sectional illustration of the positioning of the housing (60) of the battery unit (20) within the sheath (56) of the cochlear stimulator (10).

Figure 10:
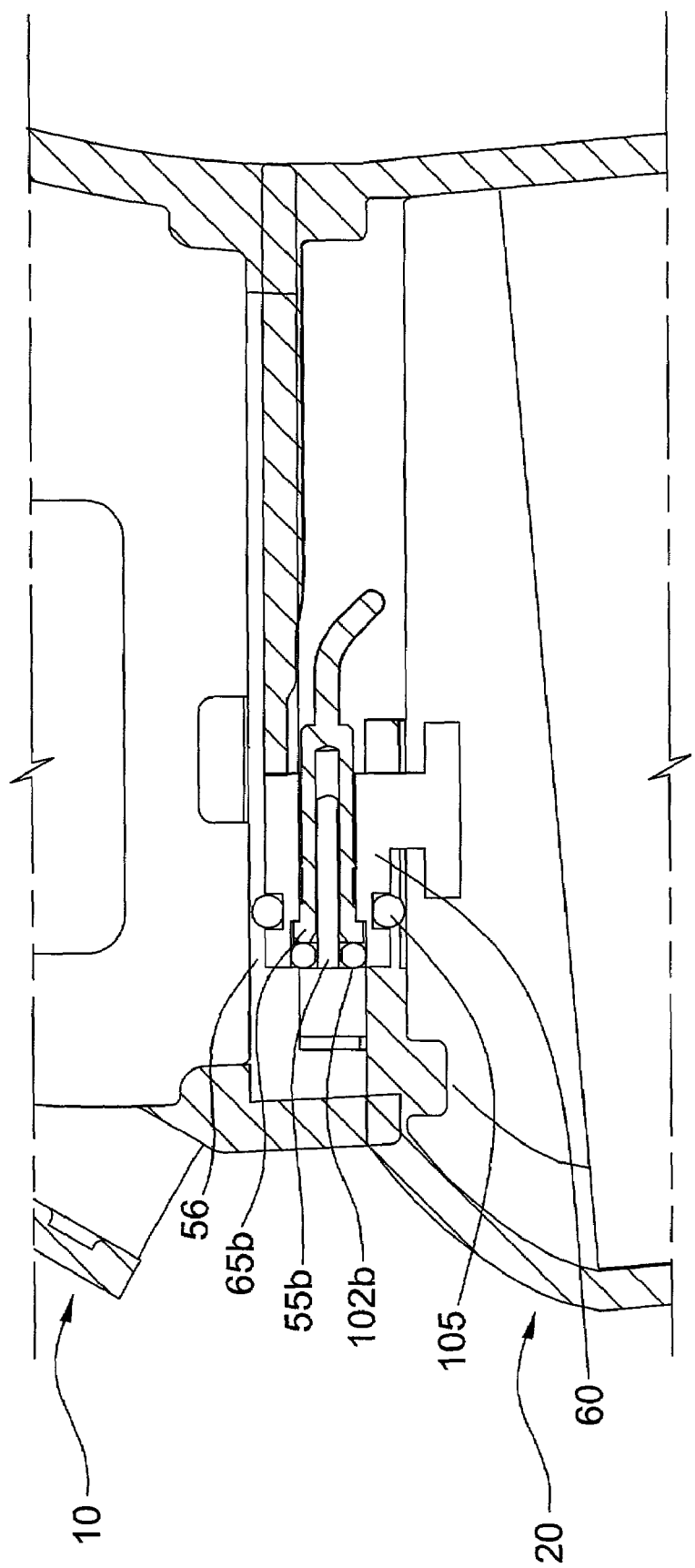
FIG. 10 is a section view from another angle of an assembled cochlear stimulator and battery unit of an alternative preferred embodiment of the present invention.
Figure 11:
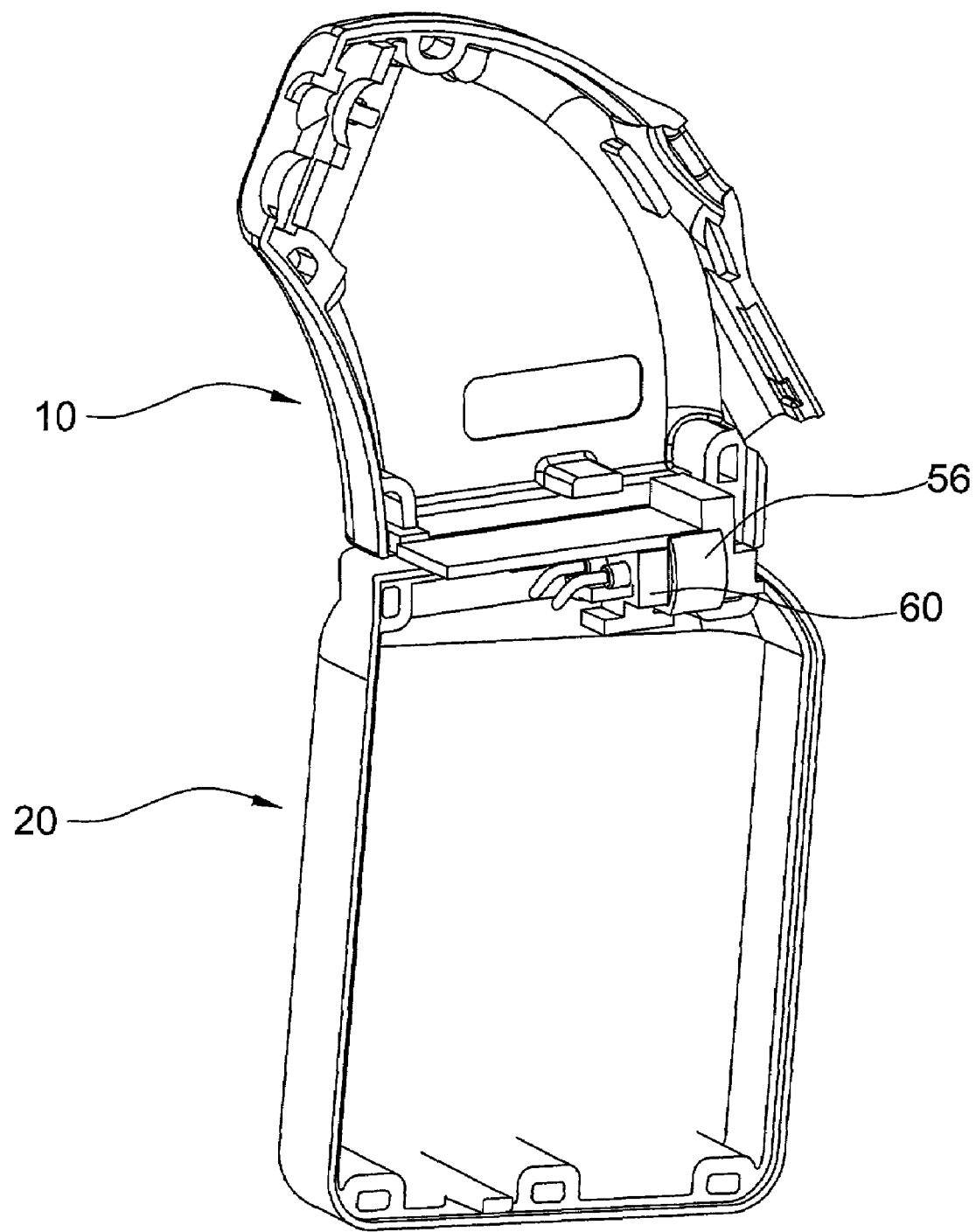
FIG. 11 is a perspective view of an assembled cochlear stimulator and battery unit of an alternative preferred embodiment of the present invention.

FIGS. 10–11 illustrate yet another embodiment of the present invention, incorporating elements of the embodiments represented by FIGS. 3–5 and FIGS. 6–9. FIG. 10 is a section view and FIG. 11 is a perspective view of an assembled cochlear stimulator (10) and battery unit (20). These figures illustrate the positioning of the entirety of the present invention after assembly, including the housing (60) having a gasket (105), the sheath (56) against which the gasket (105) seals, a terminal post (55b), and a miniature o-ring (102b), which forms a seal between terminal post (55b) and receptor socket (65b).

Figure 12:
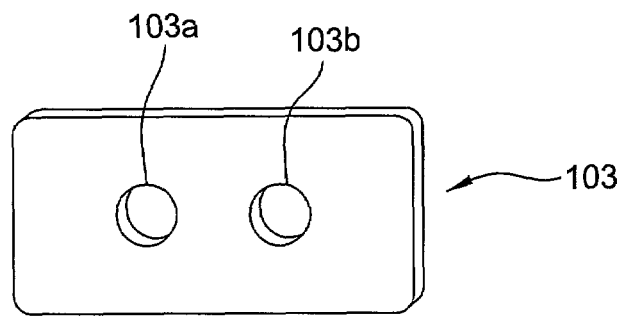
FIG. 12 is a perspective view of a plate seal of the present invention.
Figure 13:
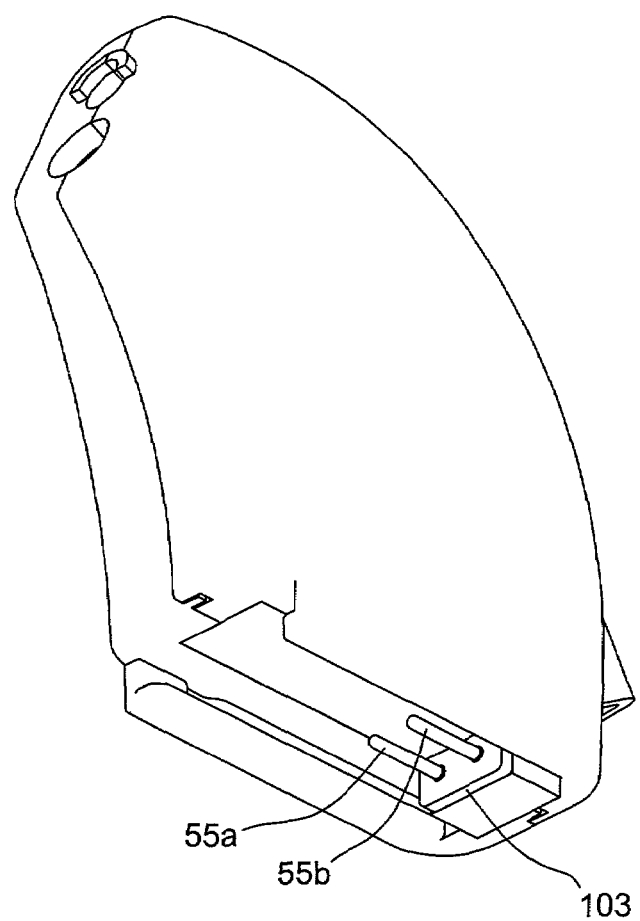
FIG. 13 is an assembly view of the plate seal of FIG. 11 installed on a cochlear stimulator.

FIG. 12 illustrates the plate seal of an alternative embodiment of the present invention. In this embodiment, a pair of holes (103a, 103b) are formed on the plate seal (103) to allow insertion of the terminal posts (55a, 55b), respectively. FIG. 13 illustrates the entirety of the cochlear stimulator (10) incorporating the plate seal (103) thereto.

Besides the illustrated application of implantable cochlear stimulators, the present invention may be used for other medical devices, such as conventional behind-the-ear hearing aids. These devices have a similar problem of sweat adversely affecting the battery and electronics. Attempts to solve this problem include covering the hearing aid with a cotton sock to absorb the sweat as described in JP11069497A2 to Honda Shizuko.

Because of the benefits and versatility conferred by the present invention, the advances set forth herein may also be used outside the field of medical devices. For example, the present invention can be used for military and police applications, such as for personal communication devices. Rather than carry around cumbersome walkie-talkies and other inefficient communication devices, a simple external, ear-mounted device can be utilized.

The present invention may also be used for portable computer and/or Internet hand-held device systems that require a seal protection and mechanical stability. Finally, the present invention can be used for personal entertainment devices leading to the ability to listen to music, news and other communications via a battery-powered device placed near a human ear or resting on the frame of a pair of glasses. For applications, medical and otherwise, where the device is exposed to sweat or other bodily fluids, but is not implanted, an inexpensive material such as buna-N nitrile rubber is preferred over the more expensive implantable materials such as implantable grade silicone rubber.

Thus, given its importance and dramatic improvements to the prior art, the present invention is needed in today's marketplace.

The invention herein has been described by examples and a particularly desired way of practicing the invention has been described. However, the invention as claimed herein is not limited to that specific description in any manner. Furthermore, the features described for one embodiment may be combined with other embodiments herein disclosed. Equivalence to the description as hereinafter claimed is considered to be within the scope of protection of this patent.

We claim:

1. A battery sealing and supporting device, comprising:
   a housing containing a microprocessor and electronic circuitry, the housing having a first slide, and a plurality of terminal posts extending from the housing;
   a battery unit having a second slide configured to be slidingly connected to the first slide, the battery unit including a plurality of terminal sockets that are each configured to receive a terminal post upon connection of the first slide and the second slide; and
   a sealing device on each of the terminal posts so as to form a seal in the terminal sockets upon connection of the first slide and the second slide.

2. The device of claim 1, wherein the electronic circuitry is cochlear stimulator circuitry.

3. The device of claim 2, wherein the battery unit includes a lithium ion battery.

4. The device of claim 1, wherein the battery unit includes a lithium ion battery.

5. The device of claim 1 wherein the seal includes a pair of miniature o-rings.

6. The device of claim 1, wherein the seal includes a plate made of elastomeric material.

7. The device of claim 1, wherein a single sealing device is common to each of the terminal posts.

8. The device of claim 1, wherein a different sealing device is positioned on each terminal post.

9. The device of claim 1, wherein the sealing device is positioned at a base of a terminal post, the base of the terminal post being where the terminal post meets the housing.

10. A battery sealing and supporting device, comprising:
    an electrical apparatus having a first slide and a plurality of terminal sockets;
    a battery unit having a second slide configured to be slidingly connected to the first slide, the battery unit including a plurality of terminal posts that are each configured to be received in a socket upon connection of the first slide and the second slide; and
    a sealing device on each of the terminal posts so as to form a seal in the terminal sockets upon connection of the first slide and the second slide.

11. The device of claim 10, wherein the seal includes a pair of miniature o-rings.

12. The device of claim 10, wherein the seal includes a plate made of elastomeric material.

13. The device of claim 10, wherein a single sealing device is common to each of the terminal posts.

14. The device of claim 10, wherein a different sealing device is positioned on each terminal post.

15. The device of claim 10, wherein the sealing device is positioned at a base of a terminal post, the base of the terminal post being where the terminal post meets a housing of the battery unit.

16. wherein the electrical apparatus is a medical device.

17. A battery sealing and supporting device, comprising:
an electrical apparatus having a first slide and a plurality of terminal posts at least partially positioned in a sheath;
a battery unit having a second slide configured to be slidingly connected to the first slide, a plug extending from the unit and configured to be inserted into the sheath upon connection of the first slide and the second slide, a plurality of sockets extending into the plug such that each terminal post is received in a different socket upon connection of the first slide and the second slide; and
a gasket positioned on the plug so as to form a seal in the sheath upon connection of the first slide and the second slide.

18. The device of claim 17, wherein the electrical apparatus is a cochlear stimulator.

19. The device of claim 18, wherein the battery unit includes a lithium ion battery.

20. The device of claim 19, and further comprising a seal mounted to the pair of terminal posts.

21. The device of claim 20, wherein the seal is a pair of miniature o-rings.

22. The device of claim 20, wherein the seal is a plate made of elastomeric material.

23. The device of claim 17, wherein the battery unit includes a lithium ion battery.

24. A battery sealing and supporting device, comprising:
an electrical apparatus having a first slide, a plug projecting from the apparatus, and a plurality of sockets extending into the plug;
a battery unit having
a second slide configured to be slidingly connected to the first slide,
a plurality of terminal posts at least partially positioned in a sheath, the sheath configured to receive the plug upon connection of the first slide and the second slide, and each terminal post configured to be received in a different socket upon connection of the first slide and the second slide; and
a gasket positioned on the plug so as to form a seal in the sheath upon connection of the first slide and the second slide.

25. The device of claim 24, wherein the electrical apparatus is a cochlear stimulator.

26. The device of claim 25, wherein the battery unit includes a lithium ion battery.

27. The device of claim 24, wherein the battery unit includes a lithium ion battery.

28. The device of claim 24, and further comprising a seal mounted to the pair of terminal posts.

29. The device of claim 28, wherein the seal is a pair of miniature o-rings.

30. The device of claim 28, wherein the seal is a plate made of elastomeric material.

31. A battery sealing and supporting device, comprising:
an electrical apparatus having a first slide, and a pair of terminal sockets positioned in a sheath;
a battery unit having
a second slide configured to be slidingly connected to the first slide,
a plug extending from the unit and being configured to be inserted into the sheath upon connection of the first slide and the second slide, and
a plurality of terminal posts extending from the plug such that each terminal post is received in a different socket upon connection of the first slide and the second slide; and
a gasket positioned on the plug so as to form a seal in the sheath upon connection of the first slide and the second slide.

32. The device of claim 31, and further comprising a seal mounted to the terminal posts.

33. The device of claim 32, wherein the seal is a pair of miniature o-rings.

34. The device of claim 32, wherein the seal is a plate made of elastomeric material.

35. A battery sealing and supporting device, comprising:
an electrical apparatus having a first slide, and a plurality of terminal sockets extending into a plug that extends from the apparatus;
a battery unit having a second slide configured to be slidingly connected to the first slide, a plurality of terminal posts at least partially positioned in a sheath, the sheath configured to receive the plug upon connection of the first slide and the second slide, and each terminal post configured to be received in a different socket upon connection of the first slide and the second slide; and
a gasket positioned on the plug so as to form a seal in the sheath upon connection of the first slide and the second slide.

36. The device of claim 35, and further comprising a seal mounted to the terminal posts.

37. The device of claim 36, wherein the seal is a pair of miniature o-rings.

38. The device of claim 36, wherein the seal is a plate made of elastomeric material.

* * * * *